United States Patent [19]
Enabnit

[11] 3,949,293
[45] Apr. 6, 1976

[54] APPARATUS AND METHOD FOR DETECTING A MOVING METAL MASS INCLUDING MEANS TO DISCRIMINATE SIGNALS HAVING A PARTICULAR PERIOD

[75] Inventor: Robert S. Enabnit, Akron, Ohio
[73] Assignee: The Goodyear Tire & Rubber Company, Akron, Ohio
[22] Filed: May 28, 1974
[21] Appl. No.: 473,643

[52] U.S. Cl. ............................... 324/41; 328/112
[51] Int. Cl.² ................... G01R 33/00; G01R 33/12
[58] Field of Search ....... 324/41, 40, 34 R; 328/112

[56] References Cited
UNITED STATES PATENTS

| | | | |
|---|---|---|---|
| 2,577,827 | 12/1951 | Tompkins | 328/112 |
| 2,648,766 | 8/1953 | Eberhard | 328/112 |
| 3,065,412 | 11/1962 | Rosenthal | 324/41 |
| 3,523,253 | 8/1970 | Moore | 328/165 |
| 3,609,563 | 9/1971 | Zinn | 328/112 |
| 3,706,027 | 12/1972 | Grice, Jr. | 324/34 R |

*Primary Examiner*—Robert J. Corcoran
*Attorney, Agent, or Firm*—F. W. Brunner; L. A. Germain

[57] ABSTRACT

In an electronic detection system, signals indicative of a detected mass of material are related to a selected mass velocity and a detection aperture through which the mass is moved. The pulse output signal from the detector, exhibiting a period related to the mass velocity and aperture length, is conditioned and enhanced as a valid detection signal while all others due to noise, etc. are rejected being outside of a selected threshold for the particular mass velocity and aperture length.

15 Claims, 6 Drawing Figures

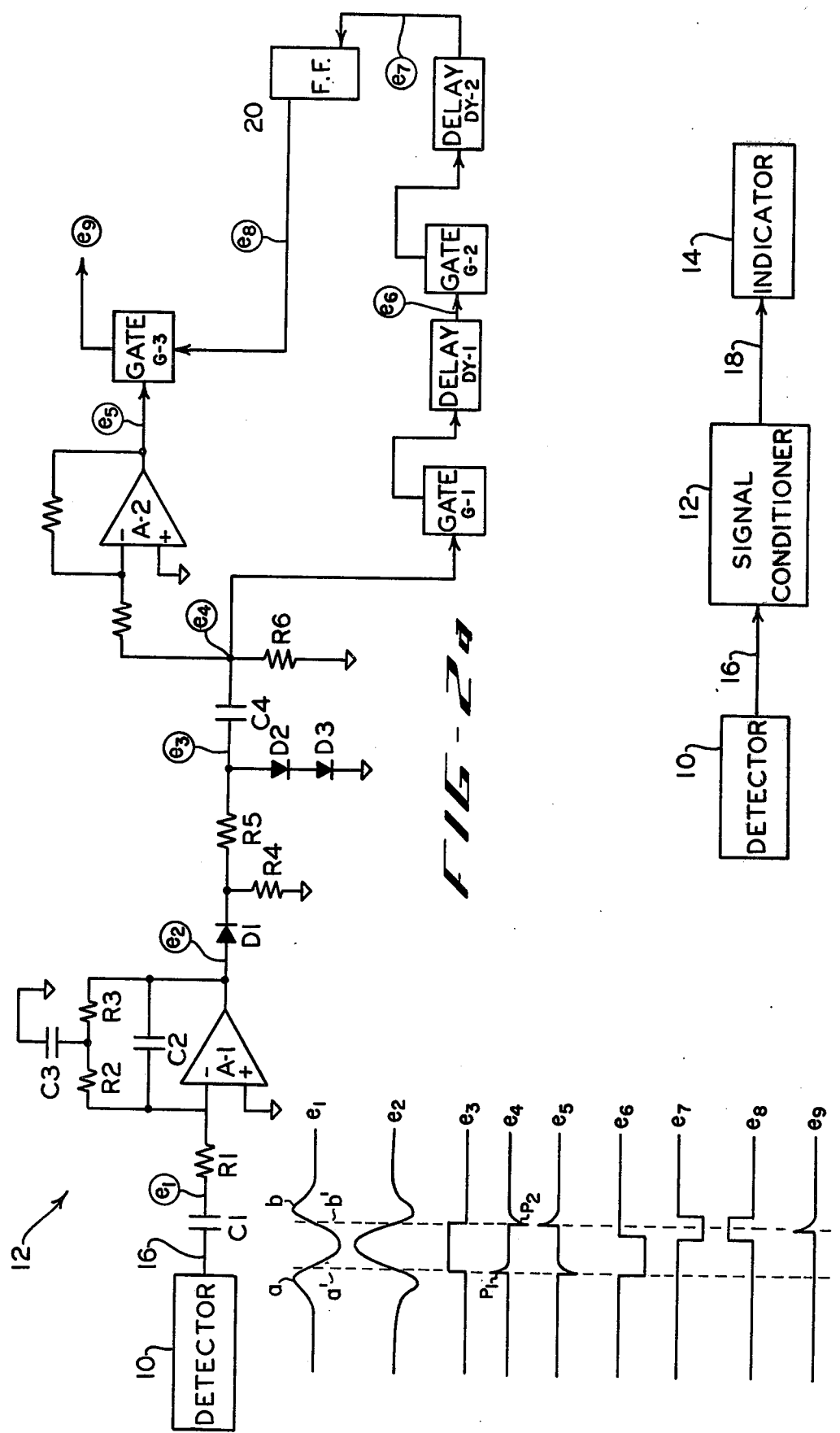

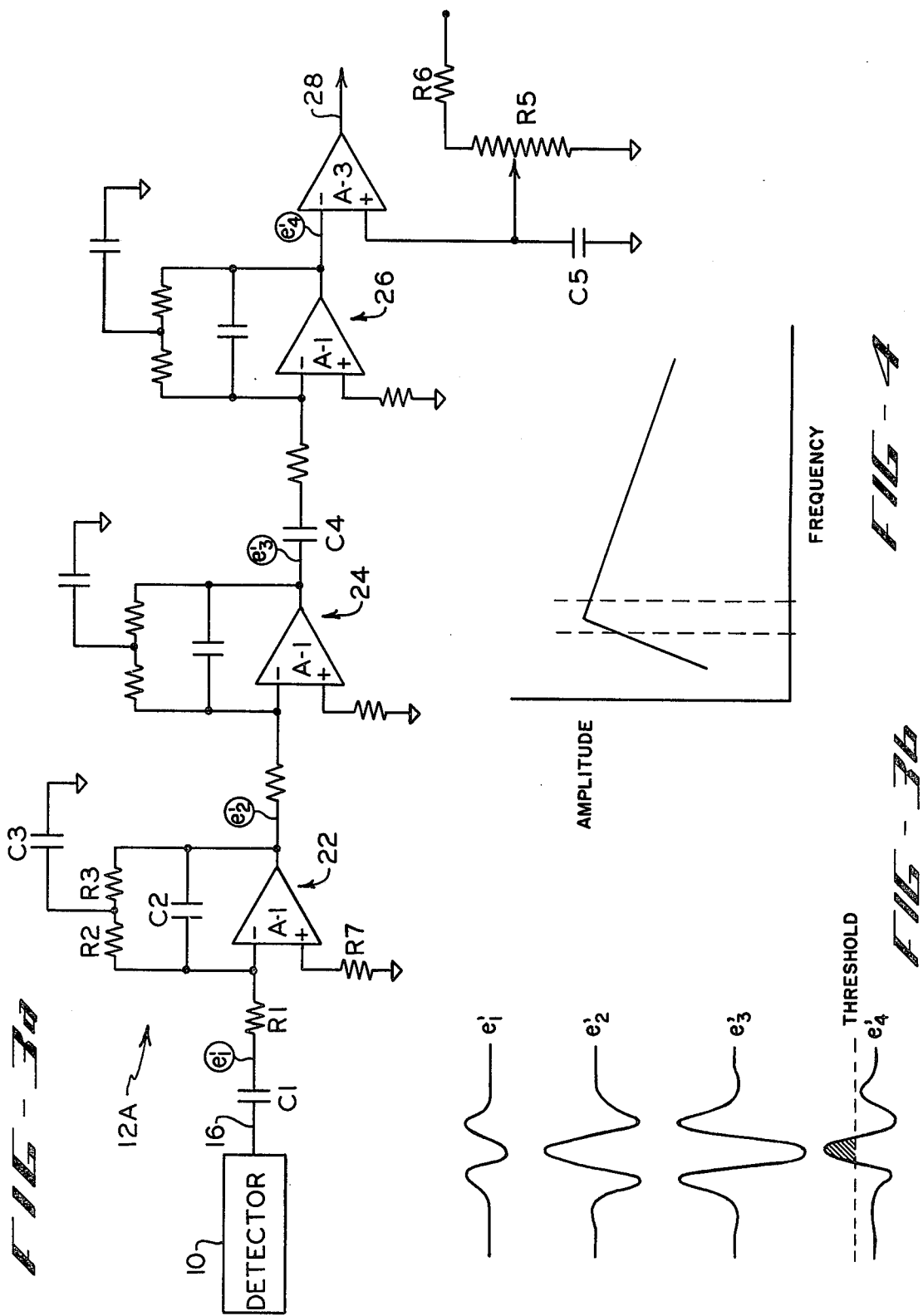

APPARATUS AND METHOD FOR DETECTING A MOVING METAL MASS INCLUDING MEANS TO DISCRIMINATE SIGNALS HAVING A PARTICULAR PERIOD

BACKGROUND OF THE INVENTION

This invention is generally concerned with electronic detection systems wherein a signal unbalance or variation, indicative of the presence of an unwanted material mass or object, generates a detection signal in a sensor for activating a warning indicator.

More specifically, the invention is concerned with optimizing detection signal discrimination by eliminating physical and environmental influences that also effect detection signals in the system.

For example, in the detection of foreign metal in a non-metallic media, the material to be tested is generally passed through an area of concentrated electromagnetic field undergoing continuous sinusoidal variation. Field variation induces eddy currents in the metal resulting in a change in the field which can be measured. Since the magnetic field decreases as the square of the distance from its source, noticeable effects on the field by metal passing through may occur primarily when this metal is in proximity to the field source. The varying magnetic field will also be affected by the metal mass, conductivity, permeability, and other physical parameters, but in simple proportion rather than exponentially. As a result, if a non-metallic material to be inspected for metal contaminants in the form of bits or pieces is carried through the varying electromagnetic field at a uniform velocity, the duration of the effect of the metal on the field is related to the field geometry or source dimensions and the metal velocity, whereas the amplitude of the effect will be more relative to physical parameters of the metal. If the material to be tested for foreign bits of metal is thus carried on a constant speed non-metallic belt conveyor, metal detection may be optimized by choosing a conveyed velocity which provides a detected metal signal duration or period differing from the period of mechanical vibration frequencies associated with the detection system, motions of other metal masses in the vicinity, electrical or electromagnetic disturbances, and other factors which cause unwanted additions to the detected signal. Optimal separation of the desired pulse from all else including random circuit noise can thus be attained by selecting only those signal pulses having a period or duration related to the belt speed and detector head geometry. This characteristic periodicity or signal duration is employed in the signal conditioning scheme that is the subject of this invention. It must be recognized, however, that the pulse-like nature of the detected signal makes customary means based on continuous sinusoidal functions, such as a narrow band pass filter where frequency = 1/period, largely ineffectual since the same frequency components appear in a variety of pulse signals and in many detectors the waveform of the detected metal pulse may change with geometry of the metal. One embodiment of the present invention employs a series of linear integrators with low pass negative feedback filters to simultaneously (a) enhance the signal pulse duration as a function of amplitude and pulse length, and (b) reduce the amplitude in proportion to duration for those pulses of greater duration than established by the metal transit time. This signal conditioning passes the minimal metal detection signal with the least modification and attenuates in proportion to deviations from that signal. Signals provided by larger metal contaminants will likewise be attenuated somewhat because of the pulse stretching action and feedback of the modified integrator but cannot be less than the minimal signal because of the original similarity in pulse lengths. The low pass negative feedback also removes slowly changing fields, drifts, etc. and provides the integrator with a zero long term reference. The linear integrator also acts to attenuate sinusoidal variations, such as produced by vibration of the detector, in proportion to their frequency by selecting a conveyor speed wherein the vibrations have a period well below the pulse period. Their attenuation relative to the signal is thus maximized. By thus sacrificing some amplitude of larger detected signal pulses, the optimum separation of desired signal and unwanted background is attained utilizing the fact that all valid detected pulses will have approximately the same period and this period will differ from the unwanted signals irrespective of amplitude. To improve the separation, the integration process may be repeated, in which case the overall characteristic of the signal conditioning means will have a sinusoidal response similar to the idealized case shown in FIG. 4 of the drawing.

SUMMARY OF THE INVENTION

The objects and advantages of the invention will become more evident from the detailed description that follows taken in conjunction with the accompanying drawing in which the method of the invention is accomplished in apparatus comprising (a) means to condition a detected pulse signal to provide an output indicative of the transit period of a mass of material traversing a detection aperture length, and (b) means to compare the conditioned signal with a threshold limit indicative of a predetermined mass velocity and aperture length.

BRIEF DESCRIPTION OF THE DRAWING

FIG. 1 is a simplified block diagram of a detection system in which the invention forms an integral part;

FIGS. 2a and 2b illustrate by schematic and waveform diagrams, respectively, the method and application of the invention;

FIGS. 3a and 3b schematically illustrate another embodiment for accomplishing the results of the invention; and FIG. 4 graphically illustrates an idealized amplitude vs. frequency plot for a continuous sinusoidal input that is closely approximated by the apparatus of FIG. 3a in achieves the method of the invention.

DESCRIPTION OF THE INVENTION

FIG 1 generally illustrates the relationship of the invention to a conventional detection system. In the drawing, an electronic detector 10 provides a demodulated detection signal 16 to a signal conditioner 12 forming the essential element of the invention. The conditioner 12, according to the teaching of this invention, improves signal discrimination in a manner such that only valid detection signals 18 are generated while all others due to noise, environmental infuences etc. are rejected. The valid detection signals 18 are then coupled to a conventional indicator 14 for an audio or visual presentation.

For the purpose of this description, it will be assumed that the material that is the subject of detection moves at a constant velocity relative to the detector. This may be accomplished in any manner including placing the material on a constant velocity conveyor moving through the detector or conversely, moving the detector at constant velocity relative to stationary subject material. In any case, a constant relative velocity exists between the detector and subject material. While other detection systems may be used to generate signals of the type $e_1$ shown in FIG. 2b, this description will be made relative to an electromagnetic field variation detector adapted to sense the presence of metal material of a minimum mass passing relative to the detector field on a constant velocity conveyor. A signal conditioner 12 that meets the needs of the invention is illustrated schematically in FIG. 2a while the waveforms associated with its operation are illustrated in FIG. 2b. Referring to the drawing, a detector 10 provides a demodulated pulse type output signal on line 16 that is indicative of a sensed condition occurrence. The signal is applied to a linear integrator A-1 through a capacitor C1 that decouples any d.c. that may be present to prevent overdriving of the amplifier should a steady state bridge unbalance exist within the detector 10. The amplifiers designated A-1 in the drawings are all type 741 op-amps as marketed by Fairchild Corporation, or other equivalent devices.

A demodulated and decoupled pulse signal due to the constant velocity passage of a detectable mass through the detector aperture exhibits a substantially constant pulse period as shown in FIG. 2b by $e_1$ with the negative going portion of the signal indicative of the metallic mass passing through detector balance. As herebefore stated, the detector field geometry is chosen such as to provide a characteristic signal periodicity or duration. The detector output signal $e_1$ is thus characterized by two pulse peaks a,b that are generated by a mass of metal passing through the detector. These two peaks are points of maximum unbalance and are separated by a period "$t$" that is determined by the detector field distribution and the rate of mass travel. Thus there is established a detector aperture length $a'$ to $b'$ determined by the field geometry and proportionally defined by the zero crossovers of the output signal $e_1$. This signal is conditioned by the integrator A-1 such that an output signal $e_2$ is provided that is proportional to the time integral of $e_1$ according to the equation $e_2 = 1/R1C2 \int e_1 dt$. The integrator A-1 operates to smooth out rapidly varying signals while a feedback low-pass filter comprising R2, R3, and C3 prevents slowly changing signals from being integrated and also establishes a long term d.c. reference. The integrated signal output $e_2$ is also inverted by A-1 and passed through a diode D1 and resistor R4 so that only the principal positive portion of the now inverted signal appears across R4.

This positive portion is clipped and limited to a constant level by diodes D2 and D3, thus providing a constant amplitude substantially square-wave pulse $e_3$ that is independent of the initial waveshape or amplitude of $e_1$ and exhibits a duration corresponding to the positive portion of the pulse and, more importantly, is related to the detector aperture length and transit duration of the detected mass through the aperture. The square wave pulse $e_3$ thus formed is differentiated by capacitor C4 and resistor R6 to provide two short duration pulses as shown in FIG. 2b at $e_4$ and designated $p_1$ and $p_2$, respectively. These pulses mark the beginning and end, respectively, of the $e_3$ pulse period. The $e_4$ signal is current amplified by an inverting follower A-2 to provide an inverted pulse $p_2$ shown at $e_5$ and of the proper polarity to activate a gate G-3. The $e_4$ pulse $p_1$ is also of the proper polarity and is used to activate a gate G-1 that operates a one-shot delay DY-1 providing a negative going pulse $e_6$ whose duration is slightly less than the period between $p_1$, $p_2$, as shown in FIG. 2b. The trailing edge or positive going portion of $e_6$ activates a second gate G-2 that operates a second one-shot delay DY-2 providing a negative going pulse $e_7$ at its output. The signal $e_7$ is a short duration pulse having a trailing edge slightly following the occurrence of $p_2$. The $e_7$ pulse is inverted by a flip-flop 20 that provides a positive going pulse $e_8$ to enable gate G-3. When the positive pulse $p_2$ from the inverter A-2 falls within the window of the gate G-3 enablement, the pulse is passed as an acceptable signal $e_9$. Longer or shorter pulse periods established by $e_3$ result in a $p_2$ pulse that misses the gate window at G-3 that is established by DY-1 and DY-2 and are therefore ignored. The output of G-3 is a signal $e_9$ that is used to activate control circuits for the indicator 14.

FIG. 3a illustrates an alternate signal conditioning configuration 12A wherein the demodulated and decoupled pulse signal $e'_1$ is operated on by a series of linear integrators 22, 24, and 26, respectively, which are similar in function and operation as herebefore described for integrator A 1 of FIG. 2a. The outputs $e'_2$, $e'_3$, and $e'_4$ of the integrators are illustrated in FIG. 3b while the idealized sinusoidal response is shown in FIG. 4.

In the drawing, integration is performed on $e'_1$ by integrator 22 via C2 and R1 in a conventional manner while a low pass negative feedback filter R2, R3, C3, provides a feedback voltage $e_f = -e_oR_2/ (1-e^{-t/R3C3})A + R2 + R3$, where A is the maximum amplitude. Resistor R7 reduces offset and improves amplifier stability. The same configuration is repeated in the following integrators 24 and 26, with C4 operating as a second d.c. decoupler to prevent the steady state level from exceeding the amplifier capacity. The integrator feedback circuits simultaneously enhance the signal pulse duration as a function of amplitude and pulse length, while reducing the amplitude in proportion to duration for those pulses of greater duration than established by the transit time of the material through the detector. The output of the series integrators is thus conditioned to the detector aperture length and mass velocity. A summing amplifier A3 compares the pulse peak amplitude to an established reference voltage from R5, R6 and if the conditioned signal peak amplitude exceeds the reference, a signal is provided on line 28 for activating an indicator 14. Capacitor C5 prevents transient comparison voltage variations from causing spurious outputs. As illustrated for the idealized sinusoidal response in FIG. 4, only those detected signals exhibiting a period within the dashed line portions of the curve will result in a valid output when the amplitude exceeds the threshold preselected for the mass velocity and aperture length. Since the period equals the reciprocal of the frequency, only detected pulses within the specified range will be accepted, all others having periods outside the range are rejected.

While certain representative embodiments and details have been shown for the purpose of illustrating the invention, it will be apparent to those skilled in the art that various changes and modifications may be made therein without departing from the spirit or scope of the invention.

What is claimed is:

1. In combination with an electronic detector adapted to provide output detection signals indicative of a variation of an electromagnetic field, the variation effected by a material mass moving at a predetermined and substantially constant relative velocity through a detection aperture as defined by the detector field geometry, and an indicator for indicating the occurrence of the field variation detected, apparatus intercoupling the detector and indicator for improving detected signal discrimination comprising:

A. signal conditioning means coupled and responsive to the detector output signal to provide a conditioned detection pulse signal having a period indicative of the transit duration as defined by a particular mass velocity and detector aperture length, said pulse period being substantially the same for all detectable materials irrespective of the material mass; and B. circuit means to compare the conditioned pulse signal with a threshold indicative of a particular predetermined reference period to provide an activation signal to said indicator.

2. Apparatus according to claim 1, wherein the signal conditioning means comprises a linear integrator having a low pass negative feedback filter to simultaneously enhance the detection signal pulse duration as a function of amplitude and pulse length and reduce the amplitude in proportion to duration for those pulses of greater duration than established by the mass transit period through the detection aperture.

3. The apparatus as set forth in claim 2, wherein the signal conditioning means further comprises:

a. means coupled and responsive to the integrator output to limit the signal amplitude and provide a square wave pulse having a period substantially corresponding to the transit period of the mass through the detector aperture; and b. means coupled and responsive to the pulse from the limiting means to differentiate the pulse such that a pair of pulses is provided that establishes the beginning and end of the detected pulse period respectively.

4. The apparatus as set forth in claim 2, wherein the means to compare comprises circuit means establishing a time oriented threshold such that a comparison is made between the pulse period of the conditioned signal and the threshold period irrespective of amplitude and only conditioned pulses that substantially correspond to the transit period of the mass through the aperture provide a valid output signal.

5. The apparatus as set forth in claim 3, wherein the means to compare comprises:

a. circuit means coupled to the differentiating means and responsive to the pulse pair to establish a gate unable pulse delayed in time to correspond to the end of the pulse period established for the mass transit duration such that the beginning of the enable pulse occurs prior to the end of the transit period while the end of the enable pulse occurs slightly after the transit period; and b. an output gate circuit coupled and responsive to the pulse pair and the gate enable pulse from the circuit means to provide an output signal when and only when the pulse indicative of the end of the detected pulse period as obtained from the differentiating means falls within the gate enable pulse period established by the above-mentioned circuit means.

6. The apparatus as set forth in claim 5, wherein the circuit means establishing a gate enable pulse comprises:

a. a first gate and a first delay circuit, said gate coupled and responsive to the pulse establishing the beginning of the detected pulse period from the differentiating means and said delay circuit coupled and responsive to said gate to provide a pulse signal at its output having a period slightly less than the mass transit period; and b. a second gate and a second delay circuit, said gate coupled and responsive to the trailing edge of the pulse output from the first delay circuit to activate said second delay circuit that responds to provide a short duration gate enable pulse having a leading edge occurring slightly before the end of the transit period and a trailing edge occurring slightly after the occurrence of the transit period.

7. Apparatus according to claim 1, wherein the signal conditioning means comprises a series of linear integrators to condition the dected signal such that all valid detection signals having substantially the same period will differ from invalid signals irrespective of signal amplitude.

8. Apparatus as set forth in claim 7, wherein the means to compare comprises circuit means establishing an amplitude threshold related to a specific mass transit period and a comparator to compare the amplitude of the conditioned output signals having a period substantially corresponding to the transit period to provide an output signal when the conditioned signal amplitude exceeds the reference.

9. In combination with an electronic detector adapted to provide output detection signals indicative of a variation in an electromagnetic field effected by a material mass moving at a preselected and substantially constant relative velocity through a detection aperture as defined by the detector field geometry and providing activating signals to an indicating device in response to the detected field variation, apparatus intercoupling the detector and indicating device for improving detected signal discrimination by establishing a detection pulse period that is substantially the same for all detectable materials irrespective of mass, comprising:

A. a linear integrator having a low pass negative feedback filter to simultaneously enhance the detection signal pulse duration as a function of amplitude and pulse length and reduce the amplitude in proportion to duration for those pulses of greater duration than established by the mass transit period through the dectection aperture;

B. means coupled and responsive to the integrator output to limit the signal amplitude and provide a square wave pulse having a period substantially corresponding to the transit period of the mass through the detector aperture;

C. means coupled and responsive to the square wave pulse from the limiting means to differentiate the pulse such that positive and negative going pulses are provided that establish the beginning and end of the detected pulse period respectively;

D. an inverting amplifier coupled to the differentiating means to invert the polarity of the pulses;

E. circuit means also coupled to the differentiating means and responsive to the pulse establishing the beginning of the pulse period to provide a positively oriented gate enable pulse delayed in time to correspond to the end of the pulse period established for a particular mass transit duration such that the beginning of the gate pulse occurs prior to the end of the transit period while the end of the gate pulse occurs slightly after the transit period;

F. an output gate circuit coupled and responsive to both the inverting amplifier output and the circuit means providing a gate enable pulse to provide an output signal when and only when the pulse indicative of the end of the detected pulse period as obtained from the differentiating means falls within the gate enable pulse period established by the above-mentioned circuit means.

10. A method of improving detected signal discrimination in an electronic detection system that provides signals indicative of a variation in an electromagnetic field effected by a material mass moving within the province of the detector field, the method comprising the steps of:

A. establishing an aperture length related to the detector field geometry;

B. moving the material through the detector aperture at a select constant velocity to provide an output pulse signal that reflects the passage duration of the material through the aperture;

C. conditioning the output signal from the detector in a manner such that the pulse period is indicative of the transit duration of the material while traversing the aperture and all detectable materials provide a pulse signal having substantially the same period irrespective of the material mass; and D. comparing the conditioned pulse to a threshold value indicative of a predetermined reference period as established by a particular material velocity and aperture length.

11. The method as set forth in claim 10, wherein the detector output signal is conditioned by an integrator circuit having a low-pass negative feedback filter circuit to simultaneously enhance the detector signal pulse duration as a function of amplitude and pulse length and reduce the amplitude in proportion to duration for those pulses of greater duration than established by the threshold value.

12. The method as set forth in claim 11, wherein the signal conditioning further comprises the steps of:

a. limiting the enhanced signal output from the integrator irrespective of the detector signal amplitude to provide a substantially square wave pulse;

b. differentiating the square wave pulse to provide a pair of pulses indicative of the beginning and end respectively of the square wave pulse period; and c. comparing the period established for the square wave pulse with a predetermined threshold period indicative of a select mass velocity and aperture length to provide an output signal when and only when the two periods substantially coincide.

13. The method as set forth in claim 12, wherein the pulse indicative of the beginning of the transit period is used to establish a gate enable pulse delayed in time to correspond to the end of the threshold period such that the beginning of the enable pulse occurs prior to the end of the select transit period for a predetermined mass velocity and aperture length while the end of the enable pulse occurs slightly after the transit period, said pulse pair coupled via a parallel branch circuit to an output gate circuit, said gate enable pulse pair subsequently coupled and compared in the output gate circuit such that enablement of the gate circuit by the gate enable pulse will provide an output signal when and only when the pulse of the pair indicative of the end of the transit period coincides in time with the output gate enablement.

14. The method as set forth in claim 10, wherein the detector output signal is conditioned in a series of linear integrator circuits having low-pass negative feedback filter circuits that simultaneosly enhance the detector signal pulse duration as a function of amplitude and pulse length, and reduce the amplitude in proportion to duration for those pulses of greater duration than established for the threshold value.

15. The method as set forth in claim 14, wherein the amplitude of the conditioned signal pulse is compared to a threshold amplitude such that an output signal is provided when the conditioned signal amplitude exceeds the threshold.

* * * * *